US010253370B2

(12) United States Patent
Albitar

(10) Patent No.: US 10,253,370 B2
(45) Date of Patent: Apr. 9, 2019

(54) HIGH-SENSITIVITY SEQUENCING TO DETECT BTK INHIBITOR RESISTANCE

(71) Applicant: Neogenomics Laboratories, Inc., Fort Myers, FL (US)

(72) Inventor: Maher Albitar, Valley Center, CA (US)

(73) Assignee: NEOGENOMICS LABORATORIES, INC., Fort Myers, FL (US)

(*) Notice: Subject to any disclaimer, the term of this patent is extended or adjusted under 35 U.S.C. 154(b) by 122 days.

(21) Appl. No.: 15/239,542

(22) Filed: Aug. 17, 2016

(65) Prior Publication Data

US 2017/0051357 A1 Feb. 23, 2017

Related U.S. Application Data

(60) Provisional application No. 62/206,248, filed on Aug. 17, 2015, provisional application No. 62/311,246, filed on Mar. 21, 2016.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 2010/0009355 A1 | 1/2010 | Kolodney |
| 2014/0249142 A1 | 9/2014 | Treon |
| 2017/0002427 A1 | 1/2017 | Albitar |

FOREIGN PATENT DOCUMENTS

| EP | 2774997 A1 | 9/2014 | |
| WO | 1996017945 A1 | 6/1996 | |
| WO | 2007100911 A2 | 9/2007 | |
| WO | 2013123031 A2 | 8/2013 | |
| WO | 2014018567 A1 | 1/2014 | |
| WO | WO2014018567 | * 1/2014 | ............... C12Q 1/68 |
| WO | 2015085075 A1 | 6/2015 | |

OTHER PUBLICATIONS

Huang Q, Wang GY, Huang JF, Zhang B, Fu WL. High sensitive mutation analysis on KRAS gene using LNA/DNA chimeras as PCR amplification blockers of wild-type alleles. Mol Cell Probes. Dec. 2010; 24(6):376-80. Epub Aug. 21, 2010. (Year: 2010).*
Huang et al. Highly sensitive KRAS mutation detection from formalin-fixed paraffin-embedded biopsies and circulating tumour cells using wild-type blocking polymerase chain reaction and Sanger sequencing. Mol Diagn Ther. Aug. 2014; 18(4):459-68. (Year: 2014).*

Liu et al. Hypermorphic mutation of phospholipase C, γ2 acquired in ibrutinib-resistant CLL confers BTK independency upon B-cell receptor activation. Blood. Jul. 2, 2015; 126(1):61-8. Epub May 13, 2015. (Year: 2015).*
Shendure J, Ji H. Next-generation DNA sequencing. Nat Biotechnol. Oct. 2008; 26(10):1135-45. (Year: 2008).*
Woyach et al. Resistance mechanisms for the Bruton's tyrosine kinase inhibitor ibrutinib. N Engl J Med. Jun. 12, 2014; 370(24):2286-94. Epub May 28, 2014. (Year: 2014).*
Woyach et al. (2014, Supplementary pp: 1-42 of N Engl J Med. 370(24):2286-94) (Year: 2014).*
Adams, RL, et al., "CpG deficiency, dinucleotide distributions and nucleosome positioning," Eur Biochem 1987, 165(1): 107-115.
Adams, RLP, et al., "Increased G+C content of DNA stabilises methyl CpG dinucleotides," Nucl Acids Res 1984, 12(14): 5869-5877.
Albitar, A. et al., "Positive Selection and High Sensitivity Test for MYD88 Mutations Using Locked Nucleic Acid," International Journal of Laboratory Hematology, Jan. 21, 2016, vol. 38, pp. 133-140.
Albitar, A. et al., High Sensitivity testing Shows Multiclonal Mutations in Patients with CLL Treated with BTK Inhibitor and Lack of Mutations in Ibrutinib-Naive Patients, Blood, Dec. 3, 2015, 126:716.
Capaldi, IB et al., "Detection of MYD88 L265P Mutations in Formalin-Fixed and Decalcified BM Biopsies from Patients with Lymphoplasmacytic Lymphoma," Experimental and Molecular Pathology, May 16, 2014, vol. 97, pp. 57-65.
Do, H, et al., "Reducing sequence artifacts in amplicon-based massively parallel sequencing of formalin-fixed paraffin-embedded DNA by enzymatic depletion of uracil-containing templates," Clin Chem 2013, 59(9), 1376-1383.
Do, H. et al., "Dramatic Reduction of Sequence Artefacts from DNA Isolated from Formalin-Fixed Cancer Biopsies by Treatment with the Uracil-DNA Glycosylase," Oncotarget, May 24, 2012, vol. 3, pp. 546-558.
Dominguez, PL et al., Wild-Type Blocking Polymerase Chain Reaction for Detection of Single Nucleotide Minority Mutations from Clinical Specimens, Oncogene, Aug. 22, 2005, vol. 24(45), pp. 6830-6834.
Gallegos-Ruiz, MI, et al., "EGFR and K-ras mutation analysis in non-small cell lung cancer: comparison of paraffin embedded versus frozen specimens," Cell Oncol 2007, 29(3): 257-264.
Honigberg, Lee A. et. al.; The Bruton tyrosine kinase inhibitor PCI-32765 blocks B-cell activation and is efficacious in models of autoimmune disease and B-cell malignancy; PNAS, Jul. 20, 2010 vol. 107, No. 29, pp. 13075-13080.
Huang, MMC et al., Highly Sensitive KRAS Mutation Detection from Formalin-Fixed Paraffin-Embedded Biopsies and Circulating Tumour Cells Using Wild-Type Blocking Polymerase Chain Reaction and Sanger Sequencing; Molecular Diagnosis & Therapy, Aug. 2014, vol. 18, No. 4, pp. 459-468.
Loiarro, M, at al., "Identification of critical residues of the MyD88 death domain involved in the recruitment of downstream kinases", J Biol Chem 2009, 284(41): 28093-28103.

(Continued)

*Primary Examiner* — Gary Benzion
*Assistant Examiner* — Olayinka A Oyeyemi
(74) *Attorney, Agent, or Firm* — Eleanor Musick; Musick Davison, LLP

(57) ABSTRACT

A method for predicting resistance to BTK inhibitors in patients with chronic lymphocytic leukemia (CLL) enhances the sensitivity of Sanger sequencing and NGS by using wild-type blocking of genes that are relevant for detecting resistance to ibrutinib. Further enhancement of sensitivity can be achieved by using cell-free DNA.

14 Claims, 8 Drawing Sheets

Specification includes a Sequence Listing.

(56) References Cited

OTHER PUBLICATIONS

Ngo, VN, et al., "Oncogenically active MYD88 mutations in human lymphoma", Nature 2011, 470(7332): 115-119.
Pasqualucci, L., et al., "Analysis of the coding genome of diffuse large B-cell lymphoma," Nat Genet 2011, 43(9): 830-837.
PCT/US2016/047404, International Search Report and Written Opinion, dated Dec. 7, 2016, 9 pgs.
PCT/US2016-040869, International Search Report and Written Opinion dated Oct. 5, 2016, 8 pages.
Salar, A., et al., 1690 MYD88 (L265P) Mutation Confers Very Poor Response and Outcome after Second-Line Therapy in Patients with Diffuse Large B-Cell Lymphoma (DLBCL), Presentation at 56th American Society of Hematology Meeting and Exposition, San Francisco, CA, 2014.
Treon, SP, et al., "MYD88 L265P somatic mutation in Waldenström's macroglobulinemia.", N Engl J Med 2012, 367(9): 826-833.
Troen, G, et al, CD79B and MYD88 Mutations in Splenic Marginal Zone Lymphoma. ISRN Oncology, 2013, 252318.
Varettoni, M, et al., "Prevalence and clinical significance of the MYD88 (L265P) somatic mutation in Waldenström's macroglobulinemia and related lymphoid neoplasms", Blood 2013, 121(13): 2522-2528.
Wang, D, et al., "508 Novel Approach to the Potential Treatment of Patients with B-Cell Lymphomas Harboring the MYD88 L265P Mutation: Combination Treatment with TLR Antagonist and Rituximab", Presentation at 56th American Society of Hematology Meeting and Exposition, San Francisco, CA, 2014.
Xu L, et al., "MYD88 L265P in Waldenström macroglobulinemia, immunoglobulin M monoclonal gammopathy, and other B-cell lymphoproliferative disorders using conventional and quantitative allele-specific polymerase chain reaction", Blood 2013, 121(11): 2051-2058.
Yost, SE, et al, "Identification of high-confidence somatic mutations in whole genome sequence of formalin-fixed breast cancer specimens," Nucleic Acids Res 2012, 40 (14).

* cited by examiner

| | BTK | PLCγ2 | BTK HS | PLCγ2 HS | Time to progression (Months) | Mutation status prior to progression (Months prior) | % CLL/ WBC |
|---|---|---|---|---|---|---|---|
| Pat # 1 | WT | WT | WT | R665W (c>t) | 23.5 | WT (12) | 7.0 |
| Pat # 2 | WT | WT | WT | R665W (c>t) | 14.9 | WT (9.4); WT (3.6) | 87.8 |
| Pat # 3 | C481S (g>c) | WT | C481S (g>c) | R665W (c>t), S707Y (c>a), L845F (a>t, a>c) | 29.1 | Mut (17) | 61.6 |
| Pat # 4 | C481R (t>c) | R665W (c>t), L845F (a>t) | C481S (g>c, t>a), C481R (t>c) | R665W (c>t), L845F (a>t) | 33.7 | WT (22.7); Mut (10.7) | 55.0 |
| Pat # 5 | C481S (g>c) | WT | C481S (g>c) | Ser707TyrdelAlaTyr (6NT deletion) | 7.2 | WT (6); WT (4.1); Mut (0.5) | 48.9 |
| Pat # 6 | WT | WT | C481S (g>c) | R665W (c>t) | 36.1 | WT (19.2); Mut (13.2) | 21.5 |
| Pat # 7 | C481S (g>c) | WT | C481S (g>c) | Ser707TyrdelAlaTyr (6NT deletion) (serum); S707Y (c>a) (plasma) | 39.3 | WT (16.3); Mut (4.7) | 75.0 |
| Pat # 8 | C481S (g>c) | WT | C481S (g>c) | WT | 37.9 | WT (14.9); Mut (2.9) | not performed |
| Pat # 9 | WT | WT | WT | WT | 8.3 | no prior testing | not performed |
| Pat # 10 | WT | WT | WT | WT | 14.5 | no prior testing | not performed |
| Pat # 11 | WT | WT | WT | WT | 37.3 | WT (1) | not performed |

Abbreviation: Pat = Patient, HS = high-sensitivity, WBC = white blood cells, WT = wild type/unmutated, Mut = mutated

FIG. 4

| | | | High-Sensitivity NGS | | Conventional NGS | |
|---|---|---|---|---|---|---|
| Patient #4 | | | | | | |
| Gene | HGVSc | HGVSp | Alternate Variant Frequency | Read Depth | Alternate Variant Frequency | Read Depth |
| PLCγ2 | NM_002661.3:c.1993C>T | NP_002652.2:p.Arg665Trp | 16.6 | 353 | 9.6 | 912 |
| PLCγ2 | NM_002661.3:c.2535A>T | NP_002652.2:p.Leu845Phe | 62.7 | 126 | 14 | 700 |
| BTK | NM_000061.2:c.1442G>C | NP_000052.1:p.Cys481Ser | 5 | 309 | 4 | 681 |
| BTK | NM_000061.2:c.1441T>A | NP_000052.1:p.Cys481Ser | 6 | 310 | 7 | 680 |
| BTK | NM_000061.2:c.1441T>C | NP_000052.1:p.Cys481Arg | 14.9 | 307 | 6 | 680 |
| Patient #6 | | | | | | |
| Gene | HGVSc | HGVSp | Alternate Variant Frequency | Read Depth | Alternate Variant Frequency | Read Depth |
| BTK | NM_000061.2:c.1442G>C | NP_000052.1:p.Cys481Ser | | | 51.2 | 697 |
| Patient #5 | | | | | | |
| Gene | HGVSc | HGVSp | Alternate Variant Frequency | Read Depth | | |
| BTK | NM_000061.2:c.1442G>C | NP_000052.1:p.Cys481Ser | 3 | 398 | | |
| Patient #15 | | | | | | |
| Gene | HGVSc | HGVSp | Alternate Variant Frequency | Read Depth | | |
| BTK | NM_000061.2:c.1442G>C | NP_000052.1:p.Cys481Ser | 2 | 89 | | |
| Patient #3 | | | | | | |
| Gene | HGVSc | HGVSp | Alternate Variant Frequency | Read Depth | | |
| BTK | NM_000061.2:c.1442G>C | NP_000052.1:p.Cys481Ser | 73.2 | 102 | | |
| PLCγ2 | NM_002661.3:c.2535A>T | NP_002652.2:p.Leu845Phe | 3 | 145 | | |
| PLCγ2 | NM_002661.3:c.2535A>C | NP_002652.2:p.Leu845Phe | 5 | 145 | | |

FIG. 5

HIGH-SENSITIVITY SEQUENCING TO DETECT BTK INHIBITOR RESISTANCE

RELATED APPLICATIONS

This application claims the benefit of the priority of U.S. Provisional Application No. 62/311,246, filed Mar. 21, 2016, and U.S. Provisional Application No. 62/206,248, filed Aug. 17, 2015, each of which is incorporated by reference in its entirety.

FIELD OF THE INVENTION

The present invention relates to methods for increasing sensitivity of sequencing for testing of genes relevant for detection of resistance to ibrutinib.

BACKGROUND

Bruton's Tyrosine Kinase (BTK) is member of the Tec family of non-receptor tyrosine kinases that is critically important for the growth, differentiation and activation of B-cells, myeloid cells, and mast cells. The BTK gene is located at cytogenetic band Xq21.33-q22 and comprises 19 exons, spanning 37 kb, encoding the full length BTK protein. The central role of BTK in B cell function is underscored by the human disease X-linked agammaglobulinemia, or Bruton's agammaglobulinemia, which is caused by loss of function mutations in BTK. These mutations result in the virtual absence of all B cells and immunoglobulins, leading to recurrent bacterial infections.

BTK is essential to B-cell receptor (BCR) signaling and in knockout mouse models, its mutation has a B cell-specific phenotype. BTK protein and mRNA are significantly overexpressed in chronic lymphocytic leukemia (CLL) compared with normal B-cells. Although BTK is not always constitutively active in CLL cells, B-cell receptor (BCR) or CD40 signaling is accompanied by effective activation of this pathway. BTK activity is involved in the disease progression of B-cell malignancies, such as Non-Hodgkin's Lymphomas, such as chronic lymphocytic leukemia (CLL), mantle cell leukemia (MCL), follicular lymphoma (FL) and diffuse large B-cell lymphoma (DLBCL), and multiple myeloma (MM).

BTK is activated by membrane localization stimulated by $PIP_3$ (phosphatidlinositol-3,4,5-triphosphate) generation and bonding to the BTK pleckstrin homology (PH) domain, and transphosphorylation of Tyr-551 by Src family kinases. Activated BTK is involved in the phosphorylation of a number of signaling molecules involved in the PLCγ (phospholipase c gamma), JNK (c-Jun NH2-terminal kinase) and p38 MAPK pathways, leading to Ca2+ mobilization, mRNA stabilization and the induction of NF-κB and AP-1 transcription factors. BTK activity is negatively regulated by a number of proteins including inhibitor of BTK (IBTK), Sab and c-Cbl. During antigenic challenge, the classical NF-κB pathway is strongly activated by B-cell receptor signaling, via formation of a "CBM" signaling complex consisting of CARD11, MALT1, and BCL10. The CBM lies downstream of PLCγ activation of BTK. The CBM pathway is pathologically altered in several lymphoma subtypes; mutations in CARD11 have been found to constitutively activate downstream NF-κB signaling.

Chronic lymphocytic leukemia (CLL) remains the most common leukemia of adults, and is incurable. Although generally considered indolent, most patients will ultimately die of the disease. Current therapies are effective in inducing initial remission in most patients who can tolerate them, but these therapies are not curative, and resistance ultimately develops.

Ibrutinib (PCI-32765 (Pharmacyclics, Sunnyvale, Calif.)) is a potent covalent kinase inhibitor that targets BTK, binding covalently to Cys-481 in the active site of BTK, resulting in inhibition of kinase activity with IC50 0.5 nM. (See J. R. Brown, PCI-32765, the First BTK (Bruton's Tyrosine Kinase) Inhibitor in Clinical Trials, *Curr Hematol Malig Rep.* 2013 March; 8(1): 1-6, incorporated herein by reference.) Ibrutinib, which has been approved by the USFDA as a treatment for mantle cell lymphoma and chronic lymphocytic leukemia, causes rapid nodal reduction and response associated with rapid increase in lymphocytosis, which then returns to baseline over time. Ibrutinib has also been demonstrated to be efficacious in certain autoimmune diseases such as arthritis and lupus. Patients with chronic lymphocytic leukemia (CLL) that develop resistance to BTK inhibitors are typically positive for histologic transformation or mutations in BTK or phospholipase c gamma 2 (PLCγ2). Mutations in BTK at the C481S hotspot alter the active site of the mutant BTK to the effect that ibrutinib is reversibly bound. PLCγ2 is downstream of BTK in the B-cell signaling pathway; mutations in PLCγ2 at either of the R665W, L845F, or S707Y hotspots result in a constitutively activated PLCγ2. (See, e.g., U.S. Patent Publ. 2015/0184249 A1, which is incorporated herein by reference.)

Bruton tyrosine kinase (BTK) inhibitors like ibrutinib have demonstrated high clinical response rates and durable remissions in patients with chronic lymphocytic leukemia (CLL) including refractory patients to conventional therapy or patients with tumor protein p53 (TP53) mutations. Patients who develop resistance to ibrutinib therapy typically have mutations in either BTK or phospholipase c γ 2 (PLCγ2). Mutations in BTK at the C481S hotspot alter the BTK binding site rendering it reversible to binding ibrutinib resulting in ineffective therapeutic results. Alternatively, mutations in PLCγ2, which is immediately downstream of BTK in the B-Cell receptor signaling pathway, result in a gain of function and BTK independent B-Cell Receptor activation. While the emergence of these mutations has been reported to be associated with resistance to therapy, little is known about the development of these resistance mutations throughout the course of therapy. In clinical trials of CLL patients on BTK inhibitor (BTKi) therapy, whole exome sequencing with next-generation sequencing (NGS) has typically been used to detect specific mutations in BTK or PLCg2 genes. Therefore, accurate, high-sensitivity assays that can be run in large volumes in a clinical setting are a necessity to further understand the relationship between the appearance of a mutation and the development of resistance to therapy and clinical progression.

Since the introduction of next-generation sequencing (NGS) technology, there has been a major transformation in the way researchers extract genetic information from biological systems, opening the way to expanded insight about the genome, transcriptome, and epigenome of any species. This ability has catalyzed a number of important breakthroughs, advancing fields from human disease research to agriculture and evolutionary science.

In principle, the concept behind NGS technology is similar to capillary electrophoresis (CE)-based Sanger sequencing: the bases of a small fragment of DNA are sequentially identified from signals emitted as each fragment is re-synthesized from a DNA template strand. NGS extends this process across millions of reactions in a massively parallel fashion, without being limited to a single or a few DNA fragments. This advance enables rapid sequencing of large strings of DNA base pairs spanning entire genomes, with the latest instruments being capable of producing hundreds of gigabases of data in a single sequencing run.

With the advent of NGS, sequencing and testing for mutations has become a standard procedure in the diagnosis and management of patients with cancer. Screening for various mutations in cancer tissue provides a means for predicting prognosis and for determining therapy. Precision medicine and targeted therapy depends on the detection of molecular abnormalities and selecting therapy that target these molecular abnormalities.

While NGS has provided a great tool for detecting mutations with a sensitivity in the range of 5%, it remains less sensitive for the detection of mutations that present in less than 5% of the analyzed DNA. This is particularly the case when attempting to analyze peripheral blood plasma. Accordingly, the need remains for method for improving the sensitivity of NGS for purposes of detecting low-occurrence mutations.

Wild-type blocking polymerase chain reaction (WTB-PCR) followed by Sanger sequencing has demonstrated high sensitivity and versatility in the detection of low percentage mutant DNA. By adding a short (10-12 mer) inaccessible [locked or bridged nucleic acid (LNA or BNA)] oligonucleotide, complementary to wild-type hotspot loci, amplification of the wild-type (WT) allele is inhibited, leading to experimentally driven positive selection for mutant alleles. Because a single nucleotide mismatch in the LNA/BNA-DNA hybrid greatly decreases its melting temperature, only mutant template DNA is free to complete its extension. Therefore, WT DNA is amplified linearly but mutant DNA is amplified exponentially. BNA is a third generation nucleic acid analog with excellent mismatch discriminating power and is considered more potent in blocking. Its strong nuclease resistant properties coupled with a 3' phosphate also prevents amplification of the wild-type DNA and selectively amplifies mutant DNA. The resulting WTB-PCR product can then be sequenced by traditional Sanger sequencing methods. We also theorized that the same principle could be applied to NGS library preparation.

While WTB-PCR/Sanger sequencing or WTB-PCR/NGS can provide accurate, high-sensitivity mutation analysis, spatial sampling bias in patients with lymphomas or CLL with few circulating tumor cells and lymph node or organ involvement could potentially lead to false negatives. This is particularly relevant when tumor heterogeneity is considered. The presence of a mutation in a subclone of the tumor cells can be easily missed if the subclone is not circulating or patchy in bone marrow—if bone marrow aspiration is used. In patients with hematologic diseases, the peripheral blood (PB) plasma has been demonstrated to be enriched for tumor-specific DNA, RNA, and proteins. This is especially true for the DNA of the more aggressive subclone. Testing cell-free DNA (cfDNA) from plasma or serum may therefore provide greater sensitivity for detecting resistance mutations than cellular DNA from PB.

In order to better understand the development of these resistance mechanisms in patients with CLL, high sensitivity testing is needed. The present invention is directed to a method for such testing.

BRIEF SUMMARY

In embodiments of the invention, a high sensitivity (HS) assay using branched and locked nucleic acids (BNA and LNA, respectively) is provided for testing for ibrutinib resistance. Methods are provided for increasing sensitivity of Sanger sequencing and NGS using wild-type blocking for two genes that are relevant for detecting resistance to ibrutinib. The two genes are BTK and PLC-γ2.

In some embodiments, sensitivity is enhanced by using peripheral blood plasma (liquid biopsy). In other embodiments, cell-free DNA was used to further enhance sensitivity.

As disclosed herein, highly sensitive Sanger and next generation sequencing strategies are described for detecting mutations in BTK and PLCγ2 based on WTB-PCR. Using this technology, we demonstrate the development of multiple resistant clones in patients with CLL treated with ibrutinib as they develop resistance to therapy.

In one aspect of the invention, a method for screening and/or monitoring a patient for a BTK inhibitor-resistant mutation includes: isolating DNA from a sample selected from bone marrow aspirate (BM), fresh peripheral blood (PB), and tissue obtained from the patient; performing PCR on the isolated DNA to produce amplified DNA while blocking amplification of wild-type DNA in a portion of the isolated DNA that encodes a BTK polypeptide and a portion of the isolated DNA that encodes a PLCγ2 polypeptide; sequencing the amplified DNA in an automated sequencer; and analyzing an output of the automated sequencer to identify mutations in the sequence. In some embodiments, amplification of wild-type DNA is blocked by a synthetic nucleotide comprising a locked nucleic acid (LNA) or a bridged nucleic acid (BNA). The LNA or BNA may be two or more of G+GA+G+G+C+A+G+C+CAT+TG-[Phosphate] (SEQ ID NO. 3), +G+A+T+T+C+CC+C+G+G/3InvdT (SEQ ID NO. 6), G+G+AC+C+T+C+CG+C+CT-[Phosphate] (SEQ ID NO. 9) and +C+T+T+A+G+G+G+T+C+TC/3InvdT (SEQ ID NO. 12), where the LNA or BNA bases are denoted as "+N" and wherein the remaining bases are ordinary DNA nucleotides. In certain embodiments, the portion of the isolated DNA that encodes a BTK polypeptide includes BTK exon 15, while the portion of the isolated DNA that encodes a PLCγ2 polypeptide includes one or more of PLCγ2 exon 19, 20 and 24. The step of sequencing may be performed using a sequencing method selected from the group consisting of Sanger sequencing, next generation sequencing, polymerase chain reaction, pyrosequencing, dye sequencing, sequencing by synthesis, and ion semiconductor sequencing. In a particularly preferred embodiment, the isolated DNA is cell-free DNA.

Further embodiments include a kit for screening, monitoring and managing a patient with a progressive B-Cell malignancy, which includes LNA or BNA oligonucleotides with two or more of SEQ ID NO. 3, SEQ ID NO. 6, SEQ ID NO. 9 and SEQ ID NO. 12. In some embodiments, the progressive B-Cell malignancy is selected from the group consisting of chronic lymphocytic leukemia (CLL), mantle cell leukemia (MCL), follicular lymphoma (FL) and diffuse large B-cell lymphoma (DLBCL), and multiple myeloma (MM).

In still another aspect of the invention, a method for high sensitivity testing for mutations in BTK and PLCγ2 includes using a wild-type (WT) blocking method of Sanger Sequencing on isolated DNA, wherein locked nucleic acids (LNA) or bridged nucleic acids (BNA) are used to block amplification of wild-type DNA in a portion of the isolated DNA that encodes a BTK polypeptide and a portion of the isolated DNA that encodes a PLCγ2 polypeptide. In certain embodiments, the LNA or BNA may be two or more of SEQ ID NO. 3, SEQ ID NO. 6, SEQ ID NO. 9 and SEQ ID NO.

12. In some implementations, the portion of the isolated DNA that encodes a BTK polypeptide includes BTK exon 15, while the portion of the isolated DNA that encodes a PLCγ2 polypeptide includes one or more of PLCγ2 exon 19, 20 and 24. In a particularly preferred embodiment, the isolated DNA is cell-free DNA.

In yet another aspect of the invention, a method for high sensitivity testing for BTK and PLCγ2 mutations includes using a wild-type blocking method of next-generation sequencing (NGS) on isolated DNA, wherein locked nucleic acids (LNA) or bridged nucleic acids (BNA) are used to block amplification of wild-type DNA in a portion of the isolated DNA that encodes a BTK polypeptide and a portion of the isolated DNA that encodes a PLCγ2 polypeptide. In certain embodiments, the LNA or BNA may be two or more of SEQ ID NO. 3, SEQ ID NO. 6, SEQ ID NO. 9 and SEQ ID NO. 12. In some implementations, the portion of the isolated DNA that encodes a BTK polypeptide includes BTK exon 15, while the portion of the isolated DNA that encodes a PLCγ2 polypeptide includes one or more of PLCγ2 exon 19, 20 and 24. In a particularly preferred embodiment, the isolated DNA is cell-free DNA.

BRIEF DESCRIPTION OF THE DRAWINGS

FIG. 4 is a table of results for tested patients suspected of clinical progression on ibrutinib therapy.

FIG. 5 is a table of results for five CLL patients tested using increased Next-Generation Sequencing (NGS) sensitivity with the addition of BNA/LNA oligonucleotides. All samples were from patients with suspected disease progression. High-sensitivity (HS) NGS includes BNA/LNA oligonucleotides in library preparation while conventional NGS does not.

DETAILED DESCRIPTION OF EMBODIMENTS

Figure 1:
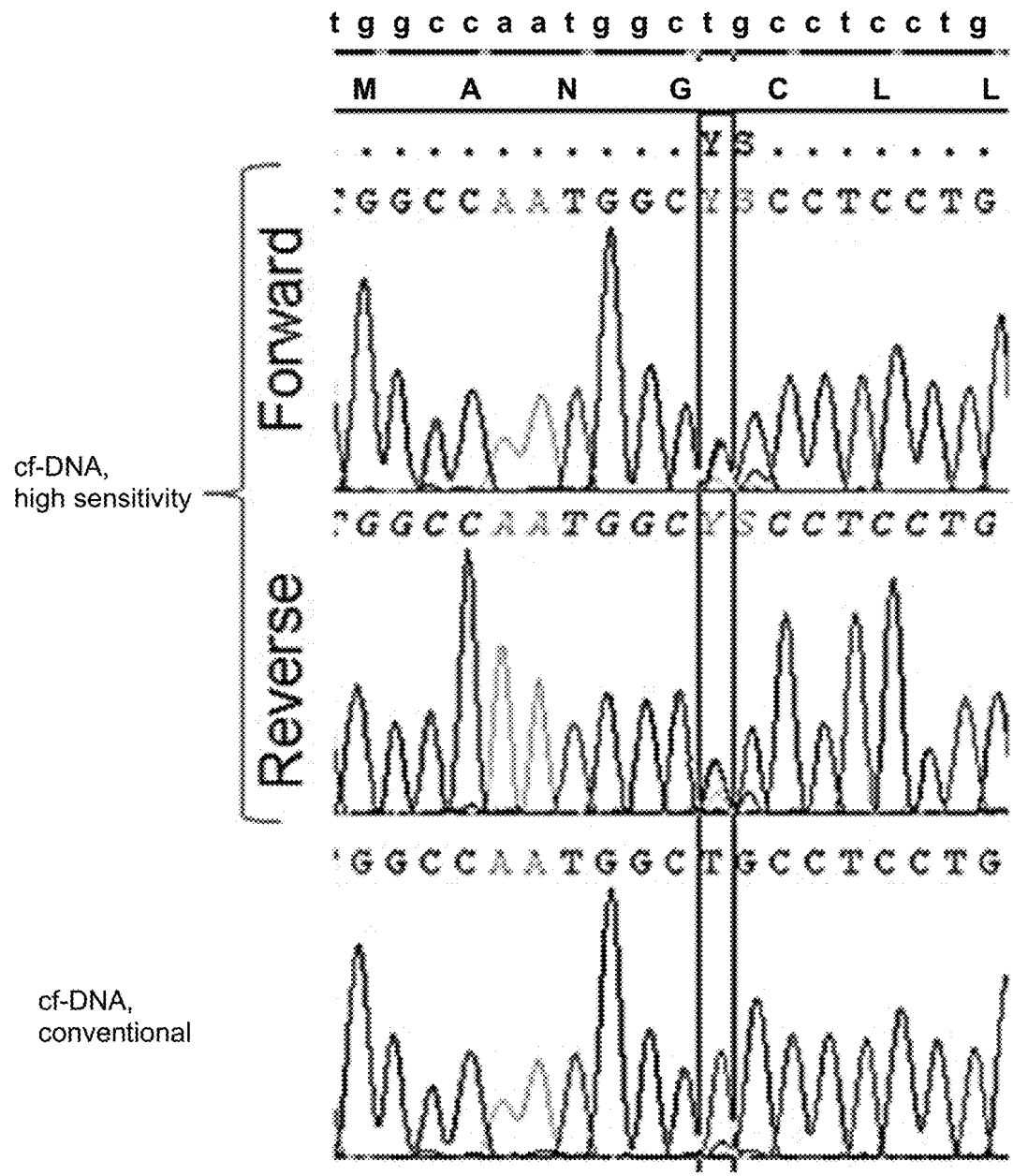
FIG. 1 is a set of chromatograms for cell-free DNA sequences (SEQ ID NO. 13) comparing sensitivity obtained using the inventive method versus conventional sequencing.
Figure 2:
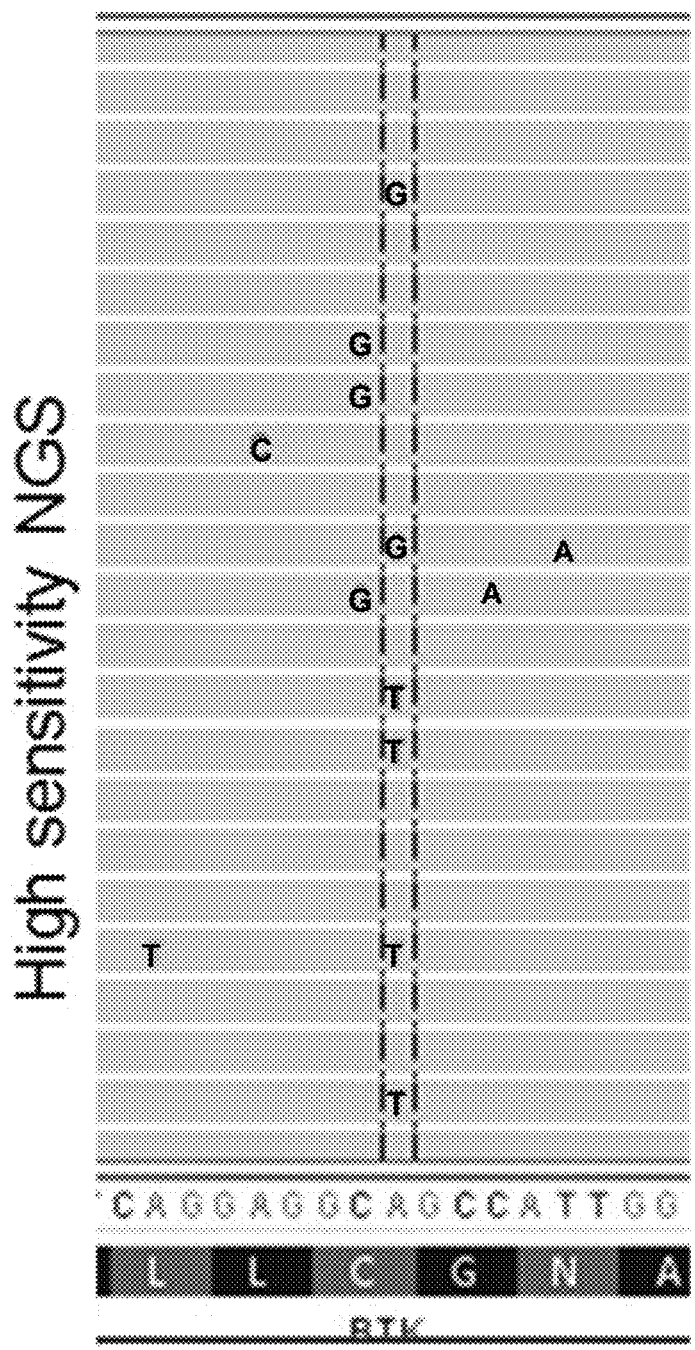
FIG. 2 shows the high sensitivity NGS results indicating the mutations in BTK (SEQ ID NO. 14).

The following description details the procedures and results for the inventive method for increasing sensitivity of Sanger sequencing and NGS through the use of wild-type blocking for two genes, BTK and PLCγ2, which are relevant for detecting resistance to ibrutinib.

The following written description and accompanying drawings identify certain gene names, accession numbers, and other identifiers that will be readily recognized by those of skill in the art as referring to information that is available via the National Center for Biotechnology Information (NCBI) public databases. Additional information contained in the NCBI databases corresponding to any identified genes, fragments, probes, amino acids, and accession numbers, including sequence listings, is incorporated herein by reference.

Definitions

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, ranges and amounts can be expressed as "about" a particular value or range. About also includes the exact amount. Generally, the term "about" includes an amount that would be expected to be within experimental error.

As used herein, a Bruton's Tyrosine Kinase (BTK) polypeptide refers to any BTK protein or polypeptide, including, but not limited to, a recombinantly produced protein, a synthetically produced protein, a native BTK protein, and a BTK protein extracted from cells or tissues. A BTK polypeptide includes wild-type BTK, allelic variant isoforms, somatic mutations including those found in tumors or hematologic malignancies, synthetic molecules from nucleic acids, protein isolated from human tissue and cells, and modified forms thereof. The BTK polypeptides provided herein can be further modified by modification of the primary amino acid sequence, by deletion, addition, or substitution of one or more amino acids. A BTK polypeptide includes any BTK polypeptide or a portion thereof having BTK activity, such as kinase activity.

As used herein, a mutant BTK polypeptide, a mutant BTK protein, a modified BTK polypeptide, or a modified BTK protein may be used interchangeably herein and refer to a BTK polypeptide that is modified at one or more amino acid positions. Exemplary modifications include, but are not limited to, substitutions, deletions or additions of amino acids.

As used herein, the term "BTK inhibitor" or "BTK antagonist" refers to an agent that inhibits or reduces at least one activity of a BTK polypeptide. BTK activities include direct and indirect activities. Exemplary direct activities include, but are not limited to, association with a target molecule or phosphorylation of a target substrate (i.e. kinase activity). Exemplary indirect activities include, but are not limited to, activation or inhibition of a downstream biological event, such as for example activation of NF-κB-mediated gene transcription.

As used herein, inhibition of BTK activity refers to any decrease in BTK activity in the presence of an inhibitor compared to the same activity in the absence of the inhibitor.

"BTK-mediated signaling" refers to any of the biological activities that are dependent on, either directly or indirection, the activity of BTK. Examples of BTK-mediated signaling are signals that lead to proliferation and survival of BTK-expressing cells, and stimulation of one or more BTK-signaling pathways within BTK-expressing cells.

A BTK "signaling pathway" or "signal transduction pathway" refers to at least one biochemical reaction, or a group of biochemical reactions, that results from the activity of BTK, and which generates a signal that, when transmitted through the signal pathway, leads to activation of one or more downstream molecules in the signaling cascade. Signal transduction pathways involve a number of signal transduction molecules that lead to transmission of a signal from the cell-surface across the plasma membrane of a cell, and through one or more in a series of signal transduction molecules, through the cytoplasm of the cell, and in some instances, into the cell's nucleus.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (e.g., phosphorothioates, phosphoroamidates). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide", peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, modification in reference to modification of a sequence of amino acids of a polypeptide or a sequence of nucleotides in a nucleic acid molecule and includes deletions, insertions, and replacements of amino acids and nucleotides, respectively.

As used herein, "next generation sequencing" or "NGS" refers to a procedure similar to capillary electrophoresis-based sequencing in which DNA polymerase catalyzes the incorporation of fluorescently labeled deoxyribonucleotide triphostphates (dNTPs) into a DNA template strand during sequential cycles of DNA synthesis. During each cycle, at the point of incorporation, the nucleotides are identified by fluorophore excitation. Instead of sequencing a single DNA fragment, the process extends across millions of fragments in a massively parallel manner.

The NGS workflow includes the basic steps of: (1) the sequencing library is prepared by random fragmentation of the DNA or cDNA sample, followed by 5' and 3' adapter ligation. Alternatively, "tagmentation" combines the fragmentation and ligation reactions into a single step to increase the efficiency of the library preparation step. Adapter-ligated fragments are then PCR amplified and gel purified; (2) for cluster generation, the library is loaded into a flow cell where fragments are captured on a law of surface-bound oligos complementary to the library adapters. Each fragment is then amplified into distinct, clonal clusters through bridge amplification. When cluster generation is completed, the templates are ready for sequencing; (3) sequencing reagents, including fluorescently labeled nucleotides, are added and the first base is incorporated. The flow cell is imaged and the emission from each cluster is recorded. The emission wavelengths and intensities are used to identify the bases; (4) newly identified sequence reads are aligned to a reference genome. After alignment, differences between the reference genome and the newly sequenced reads can be identified.

Figure 3:
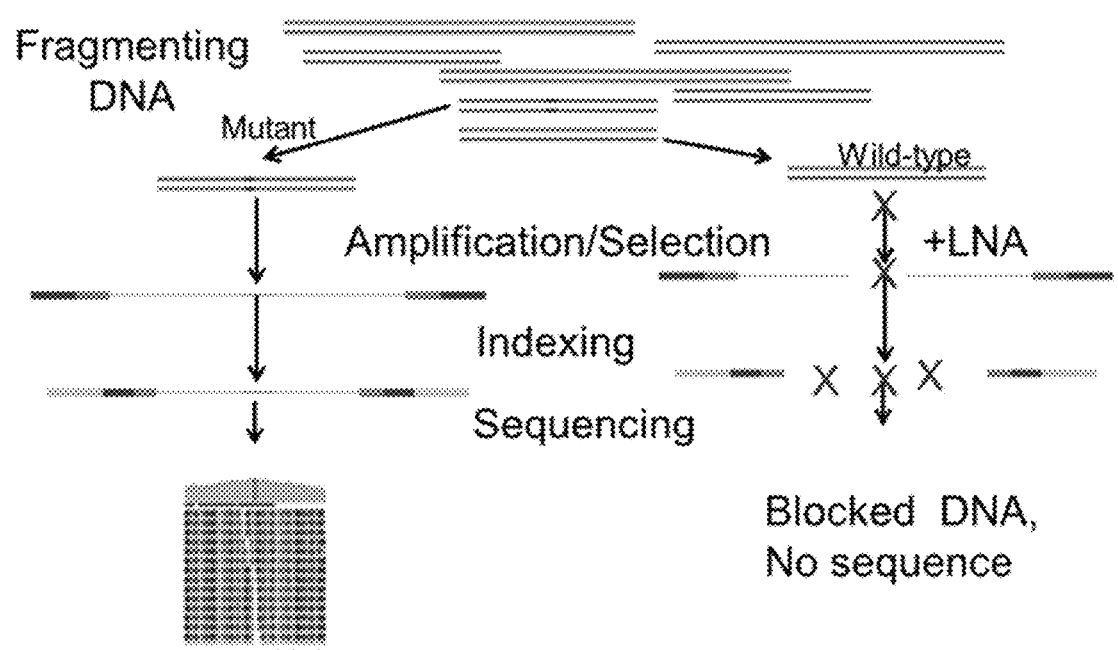
FIG. 3 illustrates the process of using LNA for selecting mutant DNA for amplicon-based NGS.

The inventive method improves sensitivity of NGS analysis by enriching the mutant DNA and reducing the relative ratio of the wild-type DNA in the analyzed sample through selective sequencing. In an exemplary embodiment, a locked nucleic acid (LNA™) probe that is identical to the wild-type is used to block the wild type DNA amplification while the mutant DNA is enriched for sequencing using amplicon-based NGS procedure. LNA™ probe is structurally different from normal DNA and when it binds to DNA, the binding is very strong and disassociating it for amplification becomes very difficult, even at high temperature, thus preventing amplification. FIG. 3 illustrates the process of using LNA for selecting mutant DNA for amplicon-based NGS.

In other embodiments, selective sequencing according to the can be achieved using techniques including ICE COLD-PCR (Improved & Complete Enrichment Co-amplification at Lower Denaturation temperature), which preferentially enriches mutant DNA sequences in an excess of wild-type DNA using an oligonucleotide complementary to wild-type sequence (RS-oligo). ICE COLD-PCR has been reported to significantly improve sensitivity in standard Sanger sequencing analysis. Another approach is the QClamp™ technology (from DiaCarta, Inc., Richmond, Calif.), which is used to screen for somatic mutations by utilizing a sequence specific wild-type template xeno-nucleic acid "Clamp" (XNA) that suppresses PCR amplification of wild-type template DNA and allows selective PCR amplification of only mutant templates. This allows the detection of mutant DNA in the presence of a large excess of wild-type template.

Additional descriptions of the HS-Sanger and HS-NGS methods are disclosed in commonly-owned U.S. patent application Ser. No. 15/134,302 and International Application No. PCT/US2016/028517, both filed Apr. 20, 2016, each of which is incorporated herein by reference in its entirety.

By employing custom BNA or LNA oligos in a wild-type blocking polymerase chain reaction, followed by sequencing using either Sanger or NGS methods, a 100× increased sensitivity was achieved relative to conventional Sanger sequencing.

Sanger sequencing was capable of detecting <1 mutant allele in background of 1000 wild-type alleles (1:1000). Similar sensitivity was achieved with HS NGS. The assay is designed to cover BTK and PLCγ2 hotspots. Using this assay, we tested peripheral blood samples from 44 Ibrutinib-naïve patients (Ib−) with CLL and 7 samples from CLL patients being treated with Ibrutinib (Ib+), which showed clinical evidence of disease progression. The same wild-type blocking was also used in NGS approach for confirmation. We performed wild-type blocking in a Nextera Rapid Capture Enrichment workflow (Illumina, Inc., San Diego, Calif.) for our custom 315 gene panel.

No BTK or PLCγ2 mutations were detected in any of the 44 ibrutinib-naïve CLL patients. In contrast, all (N=7) tested patients with progressive disease on Ibrutinib showed one or more mutation in BTK or PLCγ2 using the HS method. Without the HS testing only 4 patients (57%) showed a mutation in BTK or PLCγ2. Two patients showed multiple mutant clones. One patient with double mutations in PLCγ2 (R665W and L845F) also showed triple independent mutations in BTK at codon C481 with HS testing. These mutations give rise to two distinct mutant proteins C481R (TGC>CGC) and C481S (TGC>AGC and TGC>TCC). NGS analysis confirmed that the three BTK mutations are in three independent clones A second patient showed initially a mutation in BTK (C481S), but subsequent sample showed a mutation in PLCγ2 (R665W), in addition to the BTK mutation. All mutations detected in the peripheral blood cells were also detectable in cell-free DNA (cfDNA) using HS testing. However, without using HS testing, a BTK mutation was detected in cfDNA from a patient and this mutation was not detectable when cellular DNA was used.

The preceding results suggest that ibrutinib-naïve patients with CLL do not have BTK or PLCγ2 mutations even when a highly sensitive assay is used. Emerging BTK or PLCγ2 mutant clones can be seen after therapy with the possibility of multiple clones emerging at the same time and may involve both BTK and PLCγ2 genes in the same patient. Furthermore, testing cfDNA is not only as informative as cellular DNA, but might show mutations earlier than cellular DNA. This may have clinical relevance in patients with lymphoma when only few lymphoma cells are in circulation.

Example 1: Detecting BTK and PLCγ2 Mutations Using HS Assay

Patients and samples: Samples were collected from ibrutinib-naive CLL patients as well as from patients treated with ibrutinib as a part of the single-arm, phase-2 study of single agent ibrutinib in CLL with and without 17p deletions conducted at the NIH (NCT01500733). We tested 44 DNA samples from BTK inhibitor naïve patients with CLL by the high-sensitivity (HS) assay for mutations in BTK exon 15 and PLCγ2 Exon 19, 20 and 24. This included samples from PB (peripheral blood) (cells, plasma, and serum), bone marrow (BM) aspirate, and fresh lymph node tissue. We also tested 16 patients with CLL that were on ibrutinib therapy and had suspected resistance or disease progression. From these 16 patients we tracked the emergence of resistance mutations in BTK or PLCγ2 by both the HS and conventional assay using a total of sixty-three (63) samples collected over a 43-month period. This also included samples from PB cells (N=39), plasma (N=10), serum (N=11), and BM aspirate (N=3). All these samples were de-identified and tested according to IRB-approved protocol.

It should be noted that the procedures described herein may be specific to a particular manufacturer's/supplier's instructions. Variation to adapt these steps to kits and reagents from other sources will be readily apparent to those of skill in the art.

DNA was extracted from PB cells, BM aspirate, and fresh tissue using the QIAamp DNA Mini Kit (Qiagen; Venlo, Netherlands) in both manual and automated (QIAcube) extractions according to manufacturer's instruction: use 200 μL peripheral blood (PB) or 100 μl BM+100 μl PBS and 4 μl RNase A stock solution. Elute with 100 μl Buffer AE. Eluted DNA is collected in a standard microcentrifuge tube.

Extracted DNA was quantified using a Nanodrop 2000 (Thermo Fisher Scientific; Waltham, Mass., U.S.A.) instrument by measuring DNA concentrations using a spectrophotometer ensuring a 260 nm/280 nm ratio of approximately 1.8 (for pure DNA). If the ratio is appreciably lower, it may indicate the presence of protein, phenol, or other contaminants that could interfere with downstream applications. The DNA concentrations may be adjusted to approximately 50-100 ng/μL with water or an appropriate elution buffer.

Total nucleic acid was extracted from PB plasma and serum via the Nucli SenS EasyMAG automated platform (BioMerieux; Marcy-l'Étoile, France). DNA was then quantified using Qubit 2.0 Fluorometer (Thermo Fisher Scientific; Waltham, Mass., U.S.A.) and adjusted accordingly. Alternative procedures for DNA extraction and quantification may be used according to manufacturer's instructions.

Table 1 provides a listing of exemplary reagents useful in the procedures described herein:

TABLE 1

| Reagent | Vendor | Catalog No. | Description |
|---|---|---|---|
| 100% alcohol | VWR | 89370-084 | Histology grade; 91.5% Ethanol, 5% Isopropyl alcohol, 4.5% Methyl alcohol |
| DNAse, RNAse-free, ultra-pure water | | | |
| Ethanol Absolute | Sigma | E7023 | 200 proof, for molecular biology |
| FastStart Taq DNA polymerase (5 U/ul) | Roche | 12032937001 | With 10X concentrated PCR reaction buffer, with 20 mM MgCl2 |
| Xylene | VWR | 89370-088 | Histology grade |
| BigDye Terminator v3.1 Cycle sequencing kit | Life Technologies | 4337455 | With 5X Sequencing Buffer |
| QIAamp DNA Mini Kit | Qiagen | 51304 | Or equivalent |

Table 2 lists the BNA/LNA oligonucleotides and primers used in the inventive method.

TABLE 2

| Primer/Oligo (SEQ ID NO.) | Primer/Oligo Name | Sequence |
|---|---|---|
| A1 (1) | BTK-FW | 5'-tgt aaa acg gcc agt CAG TTG TAT GGC GTC TGC AC-3' |
| A2 (2) | BTK-REV | 5'-cag gaa aca gct atg acc TCC AGG TAT TCC ATG GCT TC-3' |
| A3 (3) | BTK-BNA | 5'-G + GA + G + G + C + A + G + C + CAT + TG-[Phosphate]-3' |
| B1 (4) | PLCγ2-Exon19-FW | 5'-tgt aaa acg gcc agt GCT CAC CTG GTC GTT TTC C-3' |
| B2 (5) | PLCγ2-Exon19-REV | 5'-cag gaa aca gct atg acc CAA GCC CCT CTG TAG AGC AT-3' |
| B3 (6) | PLCγ2-Exon19-LNA | 5'- + G + A + T + T + C + CC + C + G + G/3InvdT/-3' |
| C1 (7) | PLCγ2-Exon20-FW | 5'-tgt aaa acg gcc agt AAA AAT TGT TTG GCC ACC AG-3' |
| C2 (8) | PLCγ2-Exon20-REV | 5'-cag gaa aca gct atg acc TGG TGA ATA CTC AGA GGT TTG C-3' |
| C3 (9) | PLCγ2-Exon20-BNA | 5'-G + G + AC + C + T + C + CG + C + CT-[Phosphate]-3' |
| D1 (10) | PLCγ2-Exon24-FW | 5'-tgt aaa acg gcc agt AAA CGG TGT GCT TTG GAA AC-3' |
| D2 (11) | PLCγ2-Exon24-REV | 5'-cag gaa aca gct atg acc AGA CAG GAC CCT GTG TCA GC-3' |
| D3 (12) | PLCγ2-Exon24-LNA | 5'- + C + T + T + A + G + G + T + C + TC/3InvdT/-3' |

High-Sensitivity and Conventional Sanger DNA Sequencing:

The BTK inhibitor resistance assays were developed to amplify exon 15 of BTK and exon 19, 20 and 24 of PLCγ2. 0.25 µL Fast Start Taq DNA polymerase (Roche; Basel, Switzerland), 2.5 µL PCR reaction buffer 10× w/20 mM MgCl2, 250 µM dNTPs (Invitrogen; Waltham, Mass., U.S.A.), 0.4 µM forward primer, 0.4 µM reverse primer (IDT; Coralville, Iowa, U.S.A.) (TABLE 2), and 2 µL genomic DNA (50-100 ng/µL) were added to DNAse, RNAse-free, ultra-pure H$_2$O to create a final solution volume of 25 µL per reaction. All PCR primers were designed with a 5'-M13 sequence (M13-forward: tgt aaa acg gcc agt; M13-reverse: cag gaa aca gct atg acc) to allow for annealing of complementary sequencing primers. The HS assays were identical to their conventional counterparts except for the addition of BNA or LNA oligonucleotides A3 (SEQ ID NO. 3), B3 (SEQ ID NO. 6), C3 (SEQ ID NO. 9, D3 (SEQ ID NO. 12) (TABLE 2) being added to the master mixes of BTK and PLCγ2 Exon 19, 20, and 24, respectively. A3 (SEQ ID NO. 3) was added to the BTK master-mix at 4 µM; B3 to PLCγ2 Exon 19 at 4 µM; C3 (SEQ ID NO. 9) to PLCγ2 Exon 20 at 40 nM; D3 (SEQ ID NO. 12) to PLCγ2 Exon 24 at 4 µM. The LNA oligos were designed to feature a 3'inverted dT to inhibit both extension by DNA polymerase and degradation by 3' exonuclease. The BNA oligos were designed with a 3' phosphate for the same reason. All reactions were subjected to identical thermocycler settings; initial denaturation at 95° C. for 6 minutes; 40 cycles of denaturation at 95° C. for 30 seconds, primer annealing at 56° C. for 30 seconds, and extension at 72° C. for 1 minute 20 seconds; this was followed by a final extension at 72° C. for 10 min. PCR products were purified using Agencourt AMPure XP magnetic beads (Beckman Coulter; Brea, Calif., U.S.A.), bi-directionally sequenced using a BigDye Terminator v3.1 Cycle sequencing kit (Life Technologies; Waltham, Mass., U.S.A.), and subjected to ethanol precipitation. The precipitated DNA was then resuspended in 10 µL Hi-Di Formamide (Life Technologies; Waltham, Mass., U.S.A.), denatured at 95° C. for 3', and run on the ABI 3730XL sequencer. Sequencing data were base-called by sequencing software and analyzed by ABI Prism® SeqScape software.

In order to determine the sensitivity and limit of detection, dilution series experiments with genomic or amplicon DNA were carried out. Genomic DNA taken from samples that tested positive for BTK (C481S) or PLCγ2 (R665W) or amplicon DNA with PLCγ2 (S707Y, L845F) mutations were quantified using a Qubit dsDNA high-sensitivity assay kit (Invitrogen; Waltham, Mass., U.S.A.). This DNA was serially diluted with WT DNA of the same type.

For next-generation DNA sequencing (NGS), we applied the WTB-PCR principle to custom SureSelect QXT Target Enrichment (Agilent; La Jolla, Calif.) and Nextera Rapid Capture (Illumina, Inc., San Diego, Calif.) panels with the addition of the BNA/LNA oligonucleotides (A3 (SEQ ID NO. 3), B3 (SEQ ID NO. 6), C3 (SEQ ID NO. 9, D3 (SEQ ID NO. 12); Table 2) in order to increase our limit of detection for the hotspot mutations in hybrid-capture based NGS. A3, B3, and D3 were added to library preparation at a working concentration of 2 µM and C3 was added at 40 nM. Both panels cover 315 genes that include the BTK and PLCγ2 genes. One sample that was positive for resistance mutations in BTK and PLCγ2 was tested by Nextera Rapid Capture based assay with and without WTB-PCR in order to determine if mutant enrichment could be achieved in the NGS setting. One additional sample with resistance mutations was tested by the same assay without WTB-PCR. The SureSelect QXT Target Enrichment based assay with WTB-PCR was used on 3 additional samples with resistance mutations.

Figure 6:
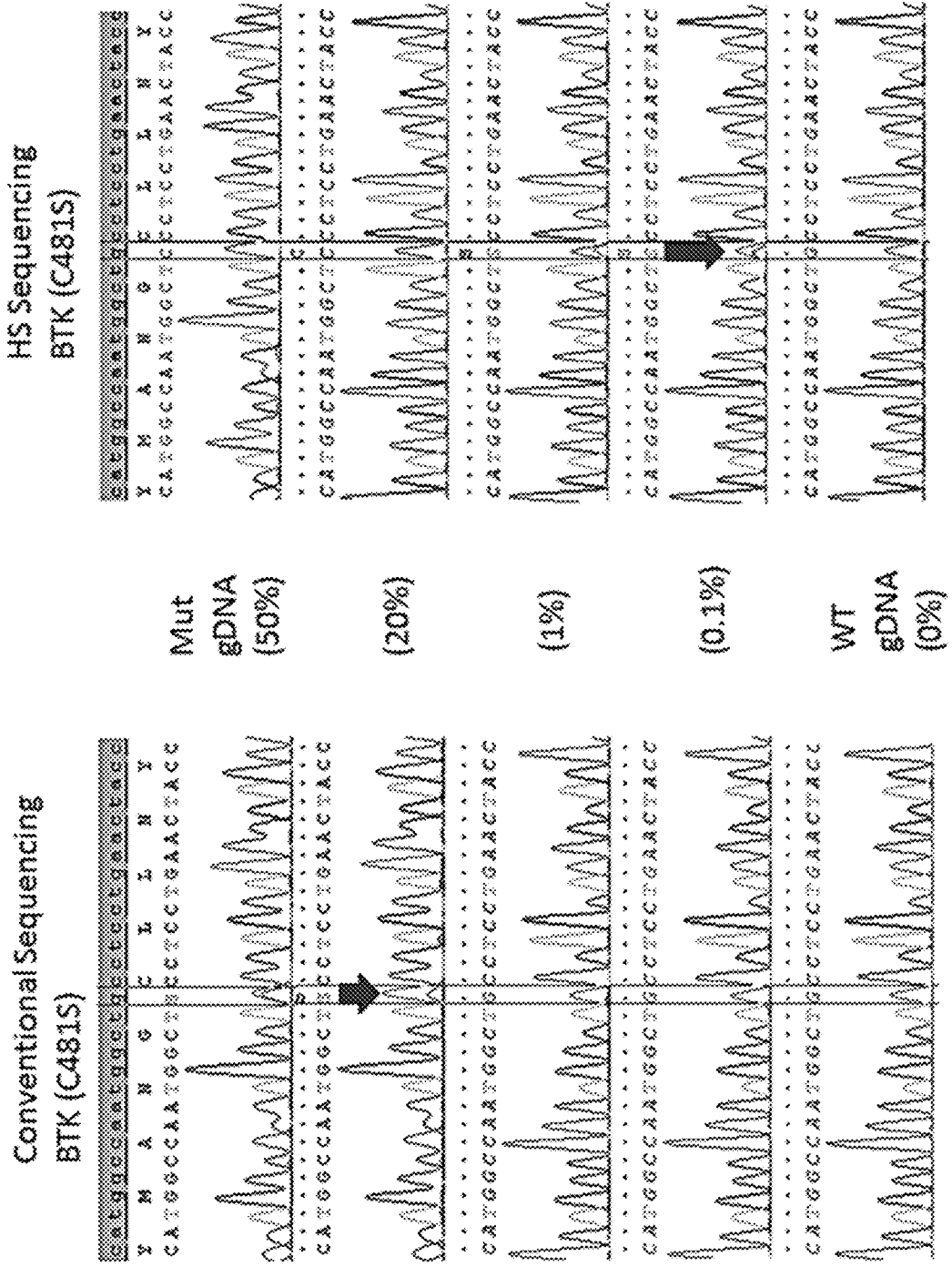
FIG. 6 is a set of chromatograms comparing conventional sequencing and HS sequencing (SEQ ID NO. 15) for detecting a BTK C481S mutation.

Results: Significant improvement of sensitivity in detecting BTK and PLCγ2 mutations using HS Assay: Using the HS assay with WTB-PCR greatly increased sequencing sensitivity when compared to the conventional assay with T-PCR. The conventional assay was able to detect approximately 15-20% mutant allele in a background of WT allele, while WTB-PCR was able to detect as low as 0.1% (FIG. 6). Similar sensitivities were obtained for the PLCγ2 sequencing, however, some loci were more amenable to positive selection by WTB-PCR than others. Sensitivities for exon 19, 20, and 24 of PLCγ2 were 0.2, 1, and 1%, respectively, mutant allele in a background of WT by HS assay.

Lack of mutation in BTK and PLCγ2 in patients with BTKi-naïve CLL: Using HS sequencing, we tested samples from 44 patients with newly diagnosed CLL or after therapy with FCR. None of these patients showed mutations in BTK exon 15 or PLCγ2 Exon 19, 20 and 24 genes.

Mutations in BTK and PLCγ2 after BTKi detected by HS: We tested 63 samples from 16 patients with CLL treated with ibrutinib who showed evidence of progression while on therapy. Using conventional Sanger sequencing, only 21% of tested samples showed mutation in BTK, while the HS testing showed mutations in 43% of tested samples (P<0.00001). Mutations in PLCγ2 were detected in 5% of tested samples using conventional Sanger sequencing and in 32% of samples using HS testing (P<0.00001). Overall, of the 16 patients on therapy with ibrutinib and suspected resistance or disease progression, 11 (69%) had a mutation in either BTK or PLCγ2, 6 (37%) patients had mutations in both genes, and 2 (12.5%) patients had three or more mutations that were detected by HS assay. By comparison, using conventional assay only 6 (37%) patients had mutations in either BTK or PLCγ2, 1 (12.5%) had mutations in both genes, and 1 (12.5%) patient had three or more mutations. By HS assay we were able to detect the emergence of resistance mutations up to 17 months prior to clinical progression. The mutations detected included BTK: C481S and C481R; PLCγ2: R665W, L845F, S707Y, P664S, P664L, Ser707TyrdelAlaTyr (6NT deletion).

Multiple subclones with BTK and PLCγ2 mutations in BTK resistant patients: Seventy-three percent of patients with CLL on ibrutinib with confirmed disease progression (n=11) as defined by iwCLL 2008 criteria had BTK or PLCγ2 mutations in one of the four exons tested. More than half of the patients with mutations (62.5%, n=8) had multiple drug resistant mutations that are detectable by the HS assay and two patients had 5 separate mutations (FIG. 4). FIG. 4 is a table comparing results in which mutational status of BTK and PLCγ2 was determined by conventional and high-sensitivity (HS) and conventional Sanger sequencing. "Time to progression" indicates the time from beginning of ibrutinib therapy to clinical progression. "Mutation status prior to progression" indicates the patients' mutational status at various time points prior to progression; the time from testing until progression is listed in months. "% CLL/WBC" indicates the percentage of CLL cells of white cell count in the tested samples as determined by flow cytometry. The fact that we were able to see three separate subclones in at least one patient (Patient #4) suggests that these other mutations also exist in separate subclones. Six of the mutations in PLCγ2 (85.7%, n=7) and one mutation in BTK (16.7%, n=6) that were detectable by HS assay at progression were undetected by conventional assay. Median percentage of CLL cells in these samples as tested at progression was 55% (n=7, range=7-87%) as determined by flow cytometry.

Next-Generation Sequencing and improvement of sensitivity using blocking oligonucleotides: In general, resistance mutations in BTK or PLCγ2 were detected in all tested samples by NGS, except for two samples: Patient #5, who had a very low frequency PLCγ2 Exon 20 6NT deletion and patient #3, who had two low frequency PLCγ2 Exon 19 R665W and Exon 20 S707Y mutations. The addition of BNA/LNA oligonucleotides enriched for BTK and PLCγ2 hotspot mutations (FIG. 5). The table in FIG. 5 provides results showing increased next-generation sequencing sensitivity with the addition of BNA/LNA oligonucleotides. All samples used were from patients with suspected progression. High-sensitivity NGS includes BNA/LNA oligonucleotides in library preparation while conventional NGS does not. In addition, NGS showed that when multiple mutations were detected in one sample, these mutations were not in tandem and were therefore present in different strands of DNA. In particular, a sample from patient #4, in which three BTK mutations were detected, the three mutations were completely independent events existing in separate DNA strands, thus suggesting different subclones.

Testing using cell-free DNA: Using HS sequencing, we performed parallel HS sequencing of 9 pairs of plasma cfDNA and cellular DNA. Of these 9 pairs, 4 parallel cfDNA isolated from serum were also tested. Of the 9 plasma cfDNA samples, 7 (78%) showed mutations in BTK and 4 (44%) showed mutations in PLCγ2. The cellular DNA showed mutations in BTK in 7 (78%) samples, but only 2 (22%) mutations were detected in the PLCγ2 gene. Of the 4 serum cfDNA samples, only 1 (25%) showed a mutation in BTK, and 1 (25%) had a mutation in PLCγ2 (see TABLE 3).

Figure 7:
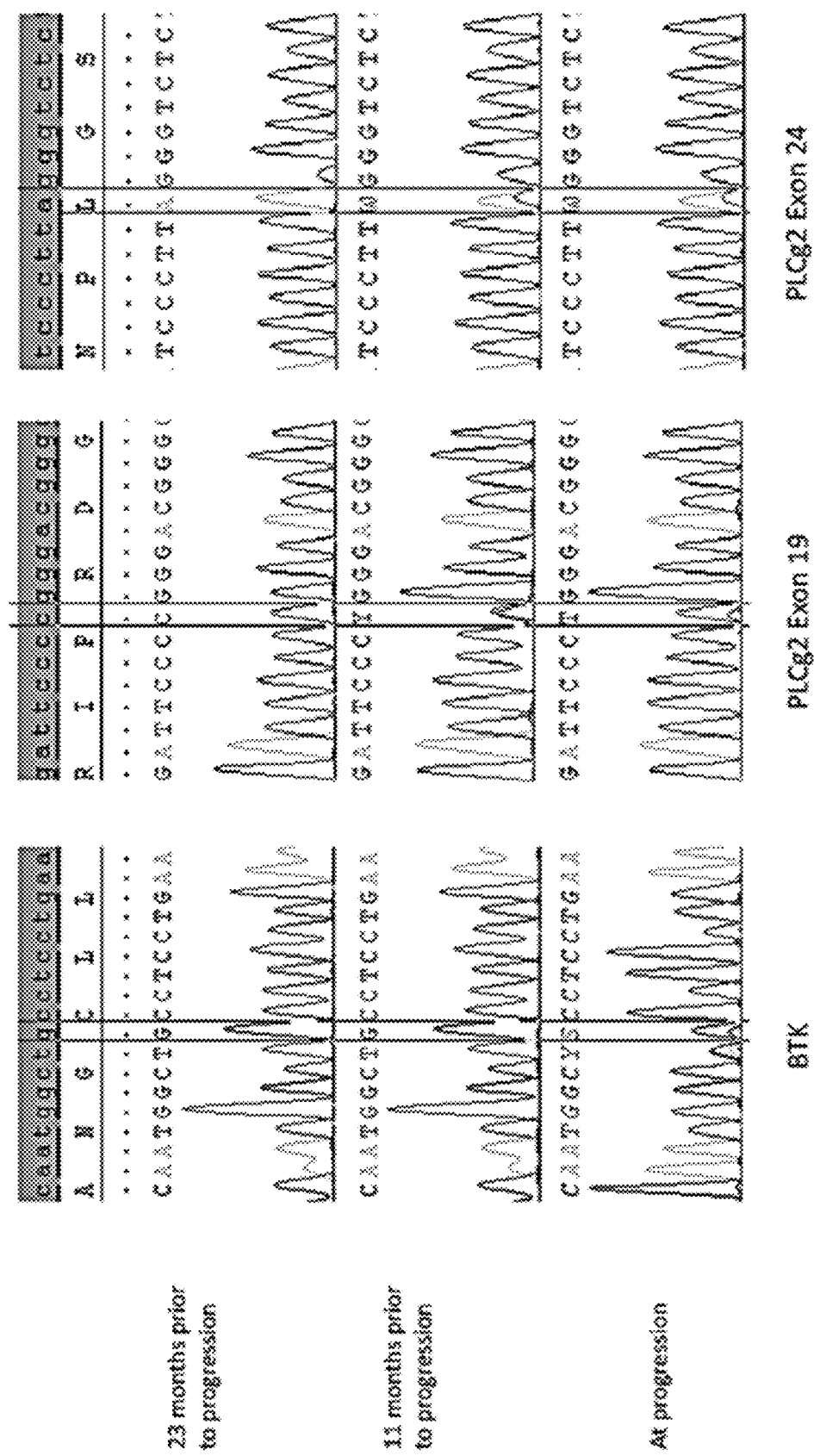
FIG. 7 is a set of chromatograms illustrating progression of three separate mutations in a single patient over time in BTK (SEQ ID NO. 16), PLCγ2 Exon 19 (SEQ ID NO. 17), and PLCγ2 Exon 24 (SEQ ID NO. 18).

Discussion: Given the association of BTK and PLCγ2 mutations with resistance to ibrutinib therapy, an accurate, highly sensitive assay—capable of being run in large volume—is a necessity. Using WTB-PCR with Sanger sequencing or NGS has multiple advantages in the clinical setting. With the HS assay resistance mutations were detected in three patients at 17, 13.2 and 12 months prior to clinical progression (FIG. 4; FIG. 7) owing to increased sensitivities of up to 0.1% mutant allele in a background of wild-type (FIG. 6). Knowing early on when resistance mutations emerge and that the majority of the time they co-develop alongside additional sub-clones with resistance mutations (FIG. 4; FIG. 7) may be very helpful in devising a strategy to overcome evolving resistance by, for example, adding additional therapeutic agents. The emergence of mutations up to 17 months prior to clinical progression may also suggest that drug resistance does not immediately follow the appearance of a resistance mutation. In that either the mutant clone is not fully resistant to therapy and might still be under a degree of negative control by the therapy or due to the relatively slow growth rate of CLL, a long time is needed for the mutant clone to become dominant and manifest as progression of the disease while on therapy.

WTB-PCR/Sanger or WTB-PCR/NGS testing allows broader coverage of mutation hot-spots and the detection of undiscovered mutations; they also provide adequate internal controls for ruling out false positives. Its additional utility in revealing low frequency mutant populations, especially in plasma cfDNA is invaluable and will guide future research.

Because we know the limit of detection for the conventional assay is approximately 15%, mutations that are detectable by HS assay but not by conventional assay are therefore present in only a small fraction of CLL cells at progression despite the relatively large percentage of CLL in the tested samples (Median=55%). The low percentage of CLL with the resistance mutations at time of progression implies that these mutations may have secondary effects on CLL cells lacking BTKi resistance mutations perhaps via tumor microenvironment resulting in ineffective therapeutic effects. Furthermore, the pattern of multiclonal BTK inhibitor resistance is unique, perhaps because of the chronic nature of the disease. In more acute malignancies, clonal evolution is typically linear with one subclone outcompeting the others and giving rise to resistance. In these cases, however, we observed that 5 of the 11 patients at progression have multiple, persisting subclones (FIG. 4; FIG. 7).

Figure 8:
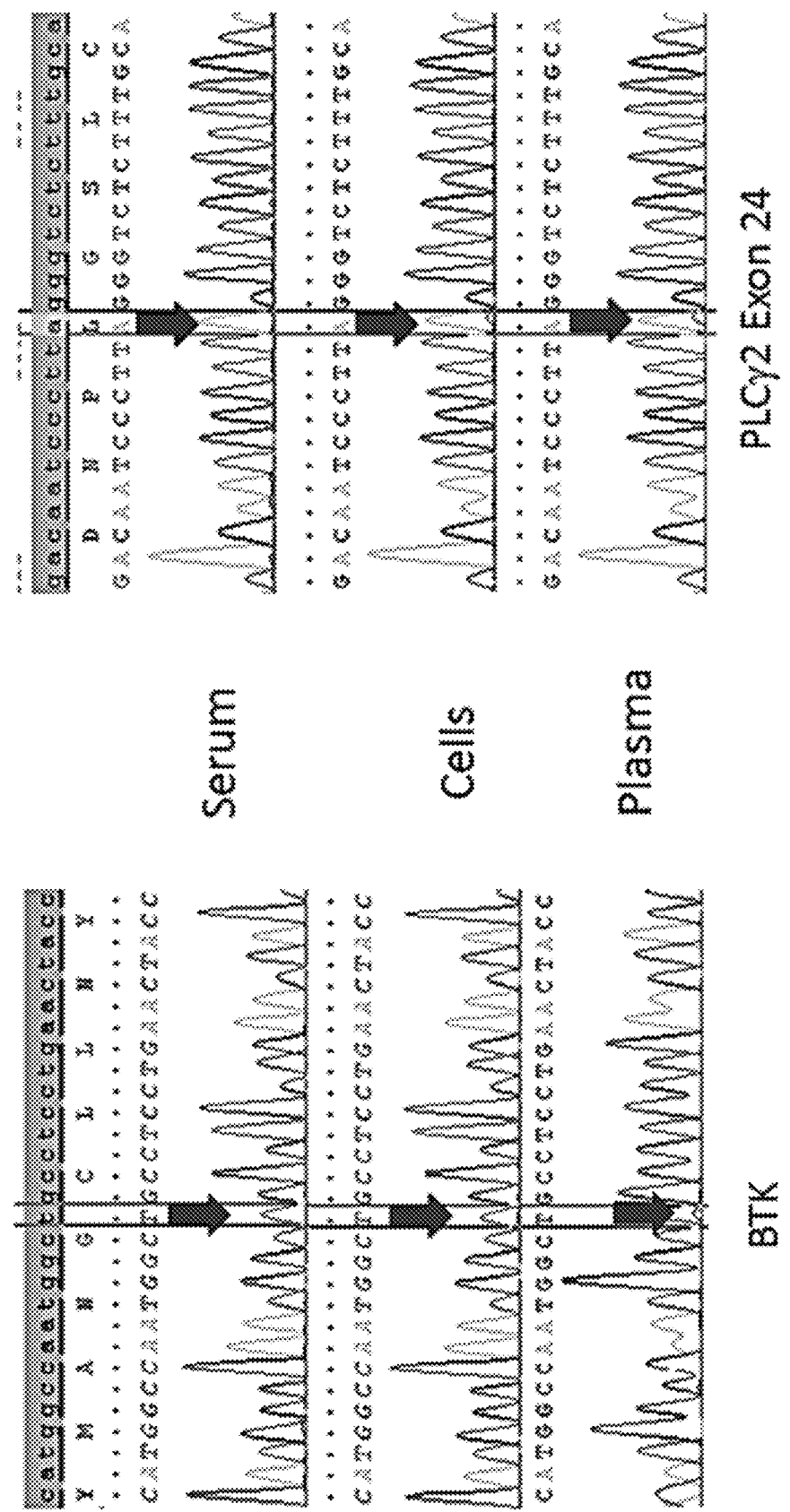
FIG. 8 is a set of chromatograms comparing results for testing of DNA derived from peripheral blood plasma (PB) with serum and cells for mutations of BTK (SEQ ID NO. 15) and PLCγ2 (SEQ ID NO. 19).

Plasma cfDNA from PB is more sensitive for detecting resistance mutations than cellular DNA or serum cfDNA. (See TABLE 3 and FIG. 8).

TABLE 3

|  | Serum | Plasma | Cells |
| --- | --- | --- | --- |
| Samples Tested | 4 | 9 | 9 |
| BTK Mutation | 1 (25%) | 7 (78%) | 7 (78%) |
| PLCγ2 Mutation | 1 (25%) | 4 (44%) | 2 (22%) |

The results provided in TABLE 3 demonstrate that cfDNA from peripheral blood plasma is more sensitive than serum and cellular DNA. High-sensitivity testing of nine temporally matched plasma and cellular samples from the same patients of which 4 serum samples were also available indicates that plasma may be enriched for tumor specific DNA more so than serum and cells. This information may be very useful in screening patients for resistance mutations, especially in patients with lymphomas or CLL with few circulating tumor cells and lymph node or organ involvement. Because the resistance mutations allow these cells to proliferate despite BTKi (BTK inhibitor) therapy, one plausible explanation for this result is that the increased proliferative rate and consequent improper processing of the cellular contents results in plasma enriched with DNA derived from CLL cells possessing resistance mutations. In serum, the coagulation process may unintentionally lyse fragile cells like granulocytes, which has the effect of diluting the serum with non-tumor cfDNA.

Example 2: Integrated Analysis of Ibrutinib Resistance in CLL

Under a phase II investigator-initiated trial (U.S. National Institutes of Health, Trial Record NCT01500733), 84 CLL patients with TP53 aberration (deletion 17p or TP53) or over age 65 were treated with 420 mg of ibrutinib daily. Inclusion criteria included histologically-confirmed diseases defines by B-lymphocytosis greater than 5000 cells/microL and immunophenotypic profile read by an expert pathologist as consistent with CLL.

Samples for patients identified as having progressive disease (PD) were tested for mutations of BTK and PLCγ2 using the WTB-PCR procedure described above.

Thirteen (13) patients, representing 15.5% of the total patients, progressed at a median follow up of 24 months. Three of four early PDs (up to 12 months) were determined to be due to histologic transformation, while eight of nine late PDs (median 34.9 months) were due to CLL. Progression-free survival (PFS) was inferior in subgroups with TP53 aberration, un-mutated IgHV (Immunoglobulin Heavy Chain Variable), advanced Rai stage, high β-2 microglobulin and relapsed/refractory disease (log-rank $p<0.05$ for all tests). Eight patients with progressive CLL were subsequently treated with small molecules targeting P13K or Bcl-2, and 6 were still alive after 15 months.

Two types of non-synonymous mutations at BTK exon 15 (C481S, C481R) and five types of non-synonymous mutations at PLCγ2 exon 19, 20 and 24 (R665W, P664S, P664L, S707Y, L845F) were identified using the WTB-PCR procedure in eight out of nine patients having progressive CLL. Concomitant BTK and PLCγ2 mutations were found in 5 out of 8 patients (62.5%). Mutations pre-dating clinical PD were identified using WTB-PCR in stored samples from six patients as early as 13 months before progression (range 1.8 to 13.0). The median time to the first detected mutation was 23.1 months (range 5.4 to 34.7). Mutational complexity increased over time as reflected by increasing types of mutations (n=3) and allele frequencies (n=3) at later time points. Both PD with progressive CLL and non-PD groups showed equivalent depth of best response in peripheral blood (PB) and bone marrow (BM) during treatment ($p>0.05$). At PD, tumor burden increased by 2- to 32-fold from nadir based on PB flow cytometry.

This study confirms the relationship between progressive CLL in ibrutinib-resistant patients and BTK and/or PLCγ2 mutations. As demonstrated in this study, because these mutations can be acquired many months before clinical progression, the ability to detect the mutations with a high degree of sensitivity can be critical to guiding therapy.

In conclusion, our data indicates that incorporating WTB-PCR into Sanger Sequencing or NGS is a highly sensitive and invaluable tool in screening and monitoring patients on ibrutinib or other BTKi therapy for resistance mutations. Additionally, plasma from peripheral blood may be more sensitive than serum and even cells in detecting the presence of these resistance mutations. Using these tools, we have also demonstrated that multiple low-frequency subclonal populations of CLL with resistance mutations in BTK and PLCγ2 emerge up to 17 months prior to clinical progression. With such knowledge, it is possible to monitor patients on BTKi therapy with increased accuracy, leading to more informed therapy decisions when mutations known to result in ineffective therapies are detected.

REFERENCES (INCORPORATED HEREIN BY REFERENCE)

1. Maddocks, K. J., et al., Etiology of Ibrutinib Therapy Discontinuation and Outcomes in Patients with Chronic Lymphocytic Leukemia. *JAMA Oncology*, 2015; 1(1), 80-87.
2. Byrd, J. C., et al., Targeting BTK with ibrutinib in relapsed chronic lymphocytic leukemia. *New England Journal of Medicine*, 2013; 369(1), 32-42.
3. Farooqui, M. Z., et al., Ibrutinib for previously untreated and relapsed or refractory chronic lymphocytic leukaemia with TP53 aberrations: a phase 2, single-arm trial. *The Lancet Oncology*, 2015; 16(2), 169-176.
4. Byrd, J. C., et al., Three-year follow-up of treatment-naive and previously treated patients with CLL and SLL receiving single-agent ibrutinib. *Blood*, 2015; blood-2014.
5. Advani, R. H., Bruton tyrosine kinase inhibitor ibrutinib (PCI-32765) has significant activity in patients with relapsed/refractory B-cell malignancies. *Journal of Clinical Oncology*, 2013; 31(1), 88-94.
6. Woyach, J. A., et al., Resistance mechanisms for the Bruton's tyrosine kinase inhibitor ibrutinib. *New England Journal of Medicine*, 2014; 370(24), 2286-2294.
7. Woyach, J. A., et al., The B-cell receptor signaling pathway as a therapeutic target in CLL. *Blood*, 2012; 120(6), 1175-1184.
8. Zhou, Q., et al., A hypermorphic missense mutation in PLCγ2, encoding phospholipase Cγ2, causes a dominantly inherited autoinflammatory disease with immunodeficiency. *American Journal of Human Genetics*, 2012; 91(4), 713-720.
9. Dominguez P L, et al, Wild-type blocking polymerase chain reaction for detection of single nucleotide minority mutations from clinical specimens. *Oncogene*, 2005; 24(45), 6830-6834.
10. Albitar, A., et al., Positive selection and high sensitivity test for MYD88 mutations using locked nucleic acid. *International Journal of Laboratory Hematology*, 2016 April; 38(2):133-140.
11. Abdur Rahman, S. M., et al., 2', 4'-BNA NC: a novel bridged nucleic acid analogue with excellent hybridizing and nuclease resistance profiles. *Nucleosides, Nucleotides, and Nucleic Acids*, 2007; 26(10-12), 1625-1628.
12. Abdur Rahman, S. M., et al., Design, synthesis, and properties of 2', 4'-BNANC: a bridged nucleic acid analogue. *Journal of the American Chemical Society*, 2008; 130(14), 4886-4896.
13. Bashashati, A., et al., Distinct evolutionary trajectories of primary high-grade serous ovarian cancers revealed through spatial mutational profiling. *Journal of Pathology*, 2013; 231(1), 21-34.
14. Campbell, P. J., et al., The patterns and dynamics of genomic instability in metastatic pancreatic cancer. *Nature*, 2010; 467(7319), 1109-1113.
15. Gerlinger, M., et al., Intratumor heterogeneity and branched evolution revealed by multiregion sequencing. *New England Journal of Medicine*, 2012; 366(10), 883-892.
16. Gerlinger, M., et al., Genomic architecture and evolution of clear cell renal cell carcinomas defined by multiregion sequencing. *Nature Genetics*, 2014; 46(3), 225-233.
17. Haffner, M. C., et al., Tracking the clonal origin of lethal prostate cancer. *Journal of Clinical Investigation*, 2013; 123(11), 4918.
18. Sottoriva, A., et al., Intratumor heterogeneity in human glioblastoma reflects cancer evolutionary dynamics. *Proceedings of the National Academy of Sciences*, 2013; 110(10), 4009-4014.
19. Manshouri, T., et al., Circulating CD20 is detectable in the plasma of patients with chronic lymphocytic leukemia and is of prognostic significance. *Blood*, 2003; 101(7), 2507-2513.
20. Rogers, A., et al., Relative increase in leukemia-specific DNA in peripheral blood plasma from patients with acute myeloid leukemia and myelodysplasia. *Blood*, 2004; 103(7), 2799-2801.
21. MA, W., et al., Plasma RNA as an alternative to cells for monitoring molecular response in patients with chronic myeloid leukemia. *Haematologica*, 2007; 92(2), 170-175.
22. MA, W., et al., Higher detection rate of JAK2 mutation using plasma. *Blood*, 2008; 111(7), 3906-3907.
23. Hallek, M., et al., Guidelines for the diagnosis and treatment of chronic lymphocytic leukemia: a report from the International Workshop on Chronic Lymphocytic Leukemia updating the National Cancer Institute—Working Group 1996 guidelines. *Blood*, 2008; 111(12), 5446-5456.
24. Anderson, K., et al., Genetic variegation of clonal architecture and propagating cells in leukaemia. *Nature*, 2011; 469(7330), 356-361.
25. Ding, L., Clonal evolution in relapsed acute myeloid leukaemia revealed by whole-genome sequencing. *Nature*, 2012; 481(7382), 506-510.

---

The invention claimed is:
1. A method for screening and/or monitoring a patient for a BTK inhibitor-resistant mutation, the method comprising:
   isolating DNA from a sample selected from bone marrow aspirate (BM), fresh peripheral blood (PB), and tissue obtained from the patient;
   performing PCR on the isolated DNA to produce amplified DNA while blocking amplification of wild-type DNA in a portion of the isolated DNA that encodes a BTK polypeptide and a portion of the isolated DNA that encodes a PLCγ2 polypeptide, wherein amplification is blocked using two or more locked nucleic acids (LNA) or bridged nucleic acids (BNA) selected from SEQ ID NO. 3, SEQ ID NO. 6, SEQ ID NO. 9, and SEQ ID NO. 12;
   sequencing the amplified DNA in an automated sequencer; and analyzing an output of the automated sequencer to identify mutations in the sequence.

2. The method of claim 1, wherein the portion of the isolated DNA that encodes a BTK polypeptide includes BTK exon 15.

3. The method of claim 1, wherein the portion of the isolated DNA that encodes a PLCγ2 polypeptide includes one or more of PLCγ2 exon 19, 20 and 24.

4. The method of claim 1, wherein the step of sequencing is performed using a sequencing method selected from the group consisting of Sanger sequencing, next generation sequencing, polymerase chain reaction, pyrosequencing, dye sequencing, sequencing by synthesis, and ion semiconductor sequencing.

5. The method of claim 1, wherein the sample comprises peripheral blood plasma.

6. A kit for screening, monitoring and managing a patient with a progressive B-Cell malignancy, the kit comprising two or more LNA or BNA oligonucleotides selected from SEQ ID NO. 3, SEQ ID NO. 6, SEQ ID NO. 9 and SEQ ID NO. 12, wherein the progressive B-Cell malignancy is selected from the group consisting of chronic lymphocytic leukemia (CLL), mantle cell leukemia (MCL), follicular lymphoma (FL) and diffuse large B-cell lymphoma (DLBCL), and multiple myeloma (MM).

7. A method for high sensitivity testing for mutations in BTK and PLCγ2, comprising using a wild-type (WT) blocking method during Sanger Sequencing on isolated DNA, wherein two or more locked nucleic acids (LNA) or bridged nucleic acids (BNA) are used to block amplification of wild-type DNA in a portion of the isolated DNA that encodes a BTK polypeptide and a portion of the isolated DNA that encodes a PLCγ2 polypeptide, wherein the two or more LNA or BNA nucleic acids are selected from SEQ ID NO. 3, SEQ ID NO. 6, SEQ ID NO. 9 and SEQ ID NO. 12.

8. The method of claim 7, wherein the portion of the isolated DNA that encodes a BTK polypeptide includes BTK exon 15.

9. The method of claim 7, wherein the portion of the isolated DNA that encodes a PLCγ2 polypeptide includes one or more of PLCγ2 exon 19, 20 and 24.

10. The method of claim 7, wherein the isolated DNA is extracted from peripheral blood plasma.

11. A method for high sensitivity testing for BTK and PLCγ2 mutations comprising using a wild-type blocking method during next-generation sequencing (NGS) on isolated DNA, wherein two or more locked nucleic acids (LNA) or bridged nucleic acids (BNA) are used to block amplification of wild-type DNA in a portion of the isolated DNA that encodes a BTK polypeptide and a portion of the isolated DNA that encodes a PLCγ2 polypeptide, wherein the two or more LNA or BNA nucleic acids are selected from SEQ ID NO. 3, SEQ ID NO. 6, SEQ ID NO. 9 and SEQ ID NO. 12.

12. The method of claim 11, wherein the portion of the isolated DNA that encodes a BTK polypeptide includes BTK exon 15.

13. The method of claim 11, wherein the portion of the isolated DNA that encodes a PLCγ2 polypeptide includes one or more of PLCγ2 exon 19, 20 and 24.

14. The method of claim 11, wherein the isolated DNA is extracted from peripheral blood plasma.

* * * * *

SEQUENCE LISTING

<160> NUMBER OF SEQ ID NOS: 19

<210> SEQ ID NO 1
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 1
tgtaaaacgg ccagtcagtt gtatggcgtc tgcac                            35

<210> SEQ ID NO 2
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 2
caggaaacag ctatgacctc caggtattcc atggcttc                         38

<210> SEQ ID NO 3
<211> LENGTH: 14
<212> TYPE: DNA
<213> ORGANISM: Artificial Sequence
<220> FEATURE:

```
<221> NAME/KEY: oligomeric compound
<223> OTHER INFORMATION: BTK BNA (G+GA+G+G+C+A+G+C+CAT+TG-[phosphate])
<220> FEATURE:
<221> NAME/KEY: misc_feature
<222> LOCATION: 2,4,5,6,7,8,9,10,13
<223> OTHER INFORMATION: locked nucleotide

<400> SEQUENCE: 3
ggaggcagcc attg                                                          14

<210> SEQ ID NO 4
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 4
tgtaaaacgg ccagtgctca cctggtcgtt ttcc                                    34

<210> SEQ ID NO 5
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 5
caggaaacag ctatgaccca agcccctctg tagagcat                                38

<210> SEQ ID NO 6
<211> LENGTH: 10
<212> TYPE: DNA
<213> ORGANISM: Artificial Sequence
<220> FEATURE:
<221> NAME/KEY: oligomeric compound
<223> OTHER INFORMATION: PLCG2 LNA (+G+A+T+T+C+CC+C+G+G/3InvdT/)
<220> FEATURE:
<221> NAME/KEY: misc_feature
<222> LOCATION: 1,2,3,4,5,6,8,9,10
<223> OTHER INFORMATION: locked nucleotide
<220> FEATURE:
<221> NAME/KEY: misc_feature
<222> LOCATION: 10
<223> OTHER INFORMATION: 3' inverted dT

<400> SEQUENCE: 6
gattccccgg                                                               10

<210> SEQ ID NO 7
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 7
tgtaaaacgg ccagtaaaaa ttgtttggcc accag                                   35

<210> SEQ ID NO 8
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 8
caggaaacag ctatgacctg gtgaatactc agaggtttgc                              40
```

```
<210> SEQ ID NO 9
<211> LENGTH: 12
<212> TYPE: DNA
<213> ORGANISM: Artificial Sequence
<220> FEATURE:
<221> NAME/KEY: oligomeric compound
<223> OTHER INFORMATION: PLCG2 LNA (G+G+AC+C+T+C+CG+C+CT-[Phosphate])
<220> FEATURE:
<221> NAME/KEY: misc_feature
<222> LOCATION: 2,3,5,6,7,8,10,11
<223> OTHER INFORMATION: locked nucleotide

<400> SEQUENCE: 9
ggacctccgc ct                                                              12

<210> SEQ ID NO 10
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 10
tgtaaaacgg ccagtaaacg gtgtgctttg gaaac                                     35

<210> SEQ ID NO 11
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 11
caggaaacag ctatgaccag acaggaccct gtgtcagc                                  38

<210> SEQ ID NO 12
<211> LENGTH: 11
<212> TYPE: DNA
<213> ORGANISM: Artificial Sequence
<220> FEATURE:
<221> NAME/KEY: oligomeric compound
<223> OTHER INFORMATION: PLCG2 LNA (+C+T+T+A+G+G+G+T+C+TC/3InvdT/)
<220> FEATURE:
<221> NAME/KEY: misc_feature
<222> LOCATION: 1,2,3,4,5,6,7,8,9,10
<223> OTHER INFORMATION: locked nucleotide
<220> FEATURE:
<221> NAME/KEY: misc_feature
<222> LOCATION: 11
<223> OTHER INFORMATION: 3' inverted dT

<400> SEQUENCE: 12
cttagggtct c                                                               11

<210> SEQ ID NO 13
<211> LENGTH: 20
<212> TYPE: DNA
<213> ORGANISM: Homo sapiens
<220> FEATURE:
<223> OTHER INFORMATION: BTK, transcript varient 3

<400> SEQUENCE: 13
tggccaatgg ctgcctcctg                                                      20

<210> SEQ ID NO 14
<211> LENGTH: 17
<212> TYPE: DNA
```

```
<213> ORGANISM: Homo sapiens
<220> FEATURE:
<223> OTHER INFORMATION: BTK, transcript varient 3

<400> SEQUENCE: 14
caggaggcag ccattgg                                              17

<210> SEQ ID NO 15
<211> LENGTH: 29
<212> TYPE: DNA
<213> ORGANISM: Homo sapiens
<220> FEATURE:
<223> OTHER INFORMATION: BTK, transcript varient 3

<400> SEQUENCE: 15
catggccaat ggctgcctcc tgaactacc                                 29

<210> SEQ ID NO 16
<211> LENGTH: 18
<212> TYPE: DNA
<213> ORGANISM: Homo sapiens
<220> FEATURE:
<223> OTHER INFORMATION: BTK, transcript varient 3

<400> SEQUENCE: 16
caatggctgc ctcctgaa                                             18

<210> SEQ ID NO 17
<211> LENGTH: 16
<212> TYPE: DNA
<213> ORGANISM: Homo sapiens
<220> FEATURE:
<223> OTHER INFORMATION: PLCG2 Exon 19

<400> SEQUENCE: 17
gattccccgg gacggg                                               16

<210> SEQ ID NO 18
<211> LENGTH: 14
<212> TYPE: DNA
<213> ORGANISM: Homo sapiens
<220> FEATURE:
<223> OTHER INFORMATION: PLCG2 Exon 24

<400> SEQUENCE: 18
tcccttaggg tctc                                                 14

<210> SEQ ID NO 19
<211> LENGTH: 25
<212> TYPE: DNA
<213> ORGANISM: Homo sapiens
<220> FEATURE:
<223> OTHER INFORMATION: PLCG2 Exon 24

<400> SEQUENCE: 19
gacaatccct tagggtctct ttgca                                     25
```